(12) United States Patent
Allen et al.

(10) Patent No.: US 8,662,791 B2
(45) Date of Patent: Mar. 4, 2014

(54) SUBTERRANEAN ALTERNATING DIGESTER SYSTEM AND METHOD

(75) Inventors: Jan Allen, Shoreline, WA (US); Thomas Kraemer, Duvall, WA (US)

(73) Assignee: Impact Bidenergy LLC, Shoreline, WA (US)

( * ) Notice: Subject to any disclaimer, the term of this patent is extended or adjusted under 35 U.S.C. 154(b) by 218 days.

(21) Appl. No.: 13/081,053

(22) Filed: Apr. 6, 2011

(65) Prior Publication Data

US 2012/0064562 A1 Mar. 15, 2012

Related U.S. Application Data

(60) Provisional application No. 61/381,304, filed on Sep. 9, 2010.

(51) Int. Cl.
*C05F 17/02* (2006.01)

(52) U.S. Cl.
USPC ............. 405/129.57; 405/129.1; 405/129.2; 405/129.55

(58) Field of Classification Search
USPC .......... 405/129.1, 129.2, 129.25, 129.55, 405/129.57; 210/605; 435/267, 290.4
See application file for complete search history.

(56) References Cited

U.S. PATENT DOCUMENTS

| | | | |
|---|---|---|---|
| 5,375,944 A * | 12/1994 | Kotani et al. | 405/129.57 |
| 5,564,862 A * | 10/1996 | Markels, Jr. | 405/129.2 |
| 5,765,437 A | 6/1998 | Farber | |
| 6,283,676 B1 * | 9/2001 | Hater et al. | 405/129.57 |
| 6,364,572 B1 * | 4/2002 | Hudgins et al. | 405/129.35 |
| 6,435,769 B2 * | 8/2002 | Harrington | 405/129.25 |
| 6,758,972 B2 * | 7/2004 | Vriens et al. | 210/605 |
| 2011/0289992 A1 | 12/2011 | Allen | |

FOREIGN PATENT DOCUMENTS

| | | |
|---|---|---|
| DE | 19719323 A1 | 11/1998 |
| EP | 0755905 A1 | 1/1997 |
| EP | 1980546 A2 | 10/2008 |
| FR | 2288719 A1 | 5/1976 |
| WO | 9946220 | 9/1999 |
| WO | 2004085019 A2 | 10/2004 |
| WO | 2006120517 A2 | 11/2006 |
| WO | 2010094024 A1 | 8/2010 |

OTHER PUBLICATIONS

Translation; EP 0755905; Bertolotto, Antonia.*
International Search Report—International Application No. PCT/US2011/051048, dated Mar. 16, 2012, together with the Written Opinion of the International Searching Authority, 12 pages.

* cited by examiner

*Primary Examiner* — Benjamin Fiorello
(74) *Attorney, Agent, or Firm* — Priya Sinha Cloutier; Lane Powell PC

(57) ABSTRACT

An alternating anaerobic and aerobic digestion system and method of forming same includes a subterranean enclosure configured to hold organic matter. The enclosure has a plurality of conduits in a bottom surface of the enclosure. The digestion system further includes an irrigation system configured to dispense a liquid from a top portion of the enclosure and to recover a percolated liquid from a bottom portion of the enclosure, a ventilation system configured to provide air flow to the bottom portion of the enclosure, and a gas-tight membrane cover configured to cover the enclosure.

27 Claims, 12 Drawing Sheets

SUBTERRANEAN ALTERNATING DIGESTER SYSTEM AND METHOD

CROSS-REFERENCE TO RELATED APPLICATIONS

The present application claims priority to U.S. Provisional Patent Application No. 61/381,304 filed Sep. 9, 2010, the disclosure of which is incorporated by reference herein in its entirety.

TECHNICAL FIELD

The invention generally relates to anaerobic digestion and aerobic digestion, commonly called composting, and more particularly the invention relates to a below grade (subterranean) system that alternates between anaerobic and aerobic conditions on a batch basis without turning or material handling during the process.

BACKGROUND ART

Current state of the art requires that both anaerobic digestion and aerobic composting processes be controlled continuously from start to finish with minimal air emissions. Additionally, anaerobic digestion is frequently followed by aerobic composting in order to convert the digestate into a commercially valuable compost or soil product. Air emissions are more significant during feedstock receiving, feedstock preparation, digestate handling, digestate land spreading, and compost pile turning (both teardown and rebuild), especially after the first stage of composting. If the process is fully enclosed through digestion and through the first stage of composting, emissions diminish significantly and are considered minimal, although not eliminated completely. Consequently, the anaerobic process and material handling operations cause the greatest emissions. Existing anaerobic systems today range from outdoor systems with no emission control to those with complete enclosure and exhaust treatment devices. The regulatory trend in North America is to regulate anaerobic digestion for the control of methane, odor, and hydrogen sulfide, and aerobic composting emissions for the control of odor, ammonia, volatile organic compounds (VOC), and/or greenhouse gases. This trend is causing an increase in the number of modified systems that utilize high solids anaerobic digestion and aerated static pile composting technologies.

Anaerobic digestion has been used in a wide range of applications on a global basis. There are millions of single-family microdigesters operating in Asia. There are approximately 100,000 low solids wastewater digesters and hundreds of medium solids manure and food processing byproduct digesters in service today. Over the past twenty five years there has been a steady increase in the development of high solids anaerobic digestion in Western and Northern Europe. Most recently this development has proven that stackable high solids organic waste from urban areas (food, paper, landscape, wood, etc.) can be digested effectively. These systems maintain temperature, physical pile structure, and moisture to facilitate fermentation and biomethane production. Aerated static pile composting was developed in 1973 by the USDA. Generally, aerated static pile composting involves a controlled aeration method, such as a piping system under the pile or piles, and a residence time of at least 14 days. Both digestion and composting generally involve grinding and then mixing the organic feedstock materials so each organic particle is relatively small. Low and medium solids systems require approximately ½ inch or less in its maximum dimension. Stackable high solids systems and composting commonly require approximately 6 inch or less in its maximum dimension. However, the cost of grinding is expensive and relatively slow so organic waste materials typically accumulate in an unprocessed and odorous state if the mass rate of incoming material is greater than the grinding rate. The cost and time requirement for grinding rises dramatically as the particle size requirement becomes smaller.

There are a number of underground digesters that are intended to minimize cost and produce usable biogas. The use of lined and covered lagoons as well as cast in place concrete plug flow systems are examples of underground digesters. However, the ability to digest un-ground high solids urban waste cost-effectively has not been possible with underground systems. There are a number of aerated static pile composting systems being practiced today to improve odor control. The use of membranes, tarps, or covers is increasing in the industry, to help limit fugitive emissions and improve moisture control. However, all of these systems still require grinding and pile turning. Because of the denseness of the feedstock material, pile depths are generally limited to between 4 feet deep and 17 feet deep.

SUMMARY OF EMBODIMENTS

In accordance with one embodiment of the invention, an alternating anaerobic and aerobic digestion system includes a subterranean enclosure configured to hold organic matter. The enclosure has a plurality of conduits in a bottom surface of the enclosure. The digestion system further includes an irrigation system configured to dispense a liquid from a top portion of the enclosure and to recover a percolated liquid from a bottom portion of the enclosure, a ventilation system configured to provide air flow to the bottom portion of the enclosure, and a gas-tight membrane cover configured to cover the enclosure. Preferably, the subterranean enclosure is water tight.

In accordance with related embodiments, the system may further include a spike configured to form air shafts in the organic matter and the spike may further include a sampling corbel on a side of the spike near its end. The ventilation system may further include an air outlet in the top portion of the enclosure and the system may further include a biofilter system in fluid communication with the air outlet of the ventilation system. The air outlet is configured to transport heat, odor, and moisture from the top portion of the enclosure to the biofilter system. The plurality of conduits may be formed by pipes placed on the bottom surface or by channels formed in the bottom surface and covered with channel cover plates. The system may further include a screw conveyor configured to dispense the organic matter into the enclosure. The screw conveyor may be coupled to a portion of the irrigation system that is configured to dispense the liquid on the pile.

In accordance with another embodiment of the invention, a method of alternating anaerobic and aerobic digestion includes providing a subterranean enclosure configured to hold un-ground or coarsely ground organic matter, covering the enclosure with a gas-tight membrane, and forming a pile of the un-ground or coarsely ground organic matter on a bottom surface of the enclosure. The bottom surface has a plurality of conduits. The method further includes dispensing a liquid on the pile and capturing biogas from a top portion of the enclosure, providing air flow to a bottom portion of the pile so that heat, odor, and moisture escape from a top portion of the pile, and inserting a spike in the pile at designated areas and times in order to form air shafts in the pile.

In accordance with related embodiments, the method may further include recovering a percolated liquid from beneath the pile and using at least a portion of the percolated liquid to dispense on the pile. The method may further include forming an air outlet in the top portion of the enclosure and forming a biofilter system in fluid communication with the air outlet, the air outlet configured to transport the heat, odor, and moisture from the top portion of the enclosure to the biofilter system. The method forming a porous, mineral aggregate layer beneath the enclosure to form a leak detection zone. The method may further include providing a screw conveyor configured to dispense the organic matter into the enclosure. The screw conveyor may also be configured to dispense the liquid on the pile. The organic matter may include oversized particles (e.g., over 6 inches). The pile may be formed with a height of at least about 20 feet. The plurality of conduits may include pipes placed on the bottom surface of the enclosure and/or channels formed in the bottom surface and covered with channel cover plates and/or a layer of pervious materials on the bottom surface of the enclosure. The organic matter may include high-carbon amendments of at least about 95% carbon and the high-carbon amendments may include cedar bark, wood, sawdust and/or paper. The method may further include taking a sample of the organic matter with the spike in order to analyze a lower portion of the pile.

In accordance with another embodiment of the invention, a method of forming an alternating anaerobic and aerobic digestion system includes providing a subterranean enclosure configured to hold organic matter, forming a plurality of conduits in a bottom surface of the enclosure, forming an irrigation system configured to dispense a liquid from a top portion of the enclosure and to recover a percolated liquid from a bottom portion of the enclosure, forming a ventilation system configured to provide air flow to the bottom portion of the enclosure, and covering the enclosure with a gas-tight membrane cover. Preferably, the subterranean enclosure is water tight.

In accordance with related embodiments, the method may further include providing a spike configured to form air shafts in the organic matter. The ventilation system may further include an air outlet in the top portion of the enclosure, and the method may further include forming a biofilter system in fluid communication with the air outlet of the ventilation system. The air outlet is configured to transport heat, odor, and moisture from the top portion of the enclosure to the biofilter system. The plurality of conduits may be formed by placing pipes on the bottom surface and/or formed by forming channels in the bottom surface and covering with channel cover plates and/or a layer of pervious materials on the bottom surface of the enclosure. The method may further include providing a screw conveyor configured to dispense the organic matter into the enclosure. The screw conveyor may be coupled to a portion of the irrigation system that dispenses the liquid on the pile. The method may further include taking a sample of the organic matter with the spike in order to analyze a lower portion of the pile.

BRIEF DESCRIPTION OF THE DRAWINGS

The foregoing features of various embodiments of the invention will be more readily understood by reference to the following detailed description, taken with reference to the accompanying drawings, in which.

DESCRIPTION OF ILLUSTRATIVE EMBODIMENTS

Various embodiments of the present invention provide a covered alternating anaerobic and aerobic digestion system and method. The method includes anaerobically digesting, and then aerated static pile composting on a batch basis without turning or material handling during the process. A pile of organic matter is formed below the land surface. The organic matter has larger, oversized particles which eliminate the need for initial grinding of the feedstock material. Operating below the land surface affords advantages in the cost of construction and in insulating the process to better control temperature. The pile is covered with a gas-tight flexible membrane cover that captures and stores the biomethane produced during digestion and captures the odors produced during composting, allowing for its subsequent treatment. The pile of organic matter is formed on a lower floor or bottom surface of a subterranean enclosure. The bottom surface has a plurality of conduits, such as pipes or channels, for both the collection of liquid percolation during digestion and forced aeration during composting. These air and liquid conduits are located and designed so as to serve both of these functions at different times. Below this bottom surface is a space and lower chamber surface of the digestion system for the exclusion of groundwater and the collection and recovery of any fluid leakage, commonly called a leak detection zone. Details of illustrative embodiments are discussed below.

Figure 1:
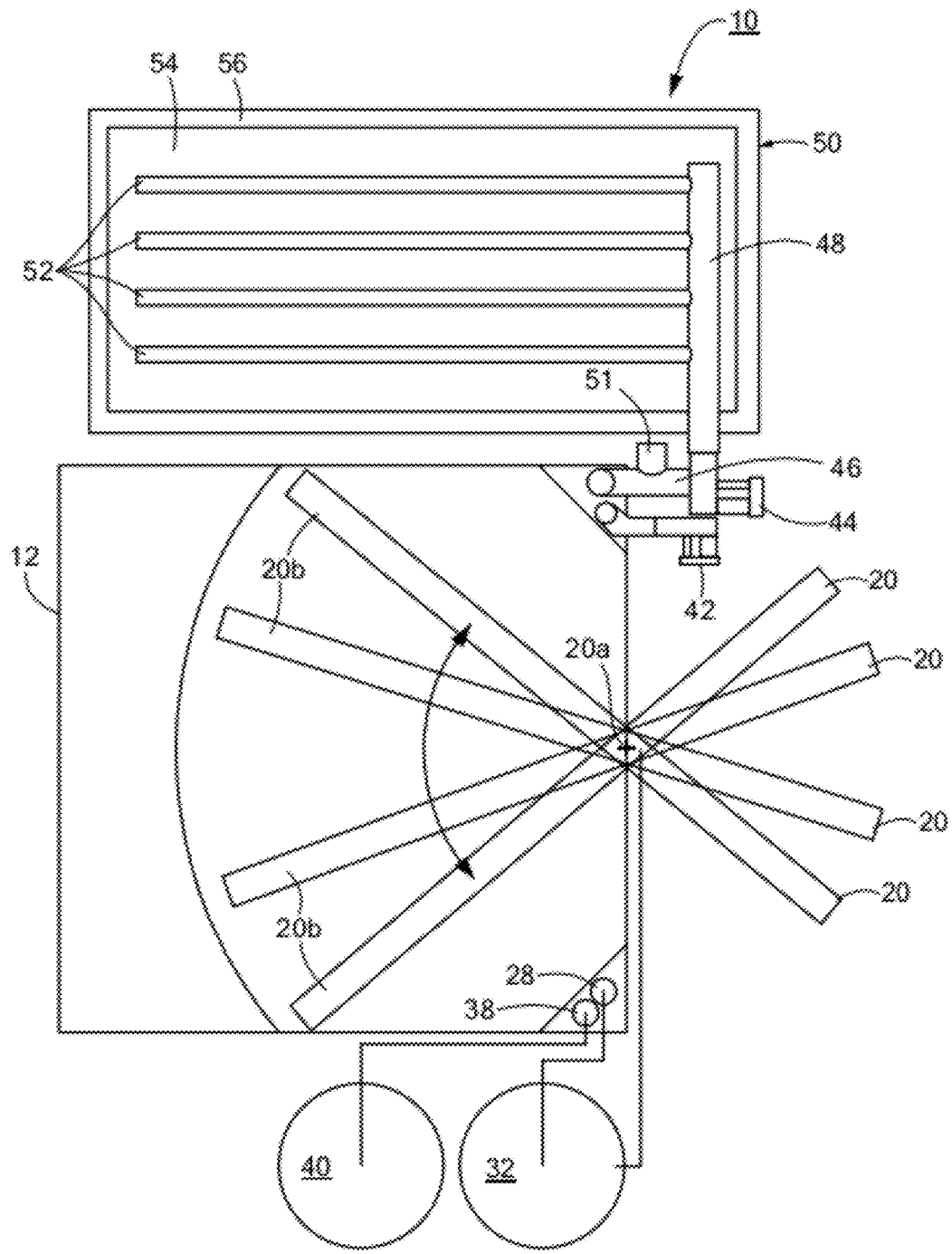
FIG. 1 shows a plan view of a subterranean alternating digester system according to embodiments of the present invention.
Figure 2:
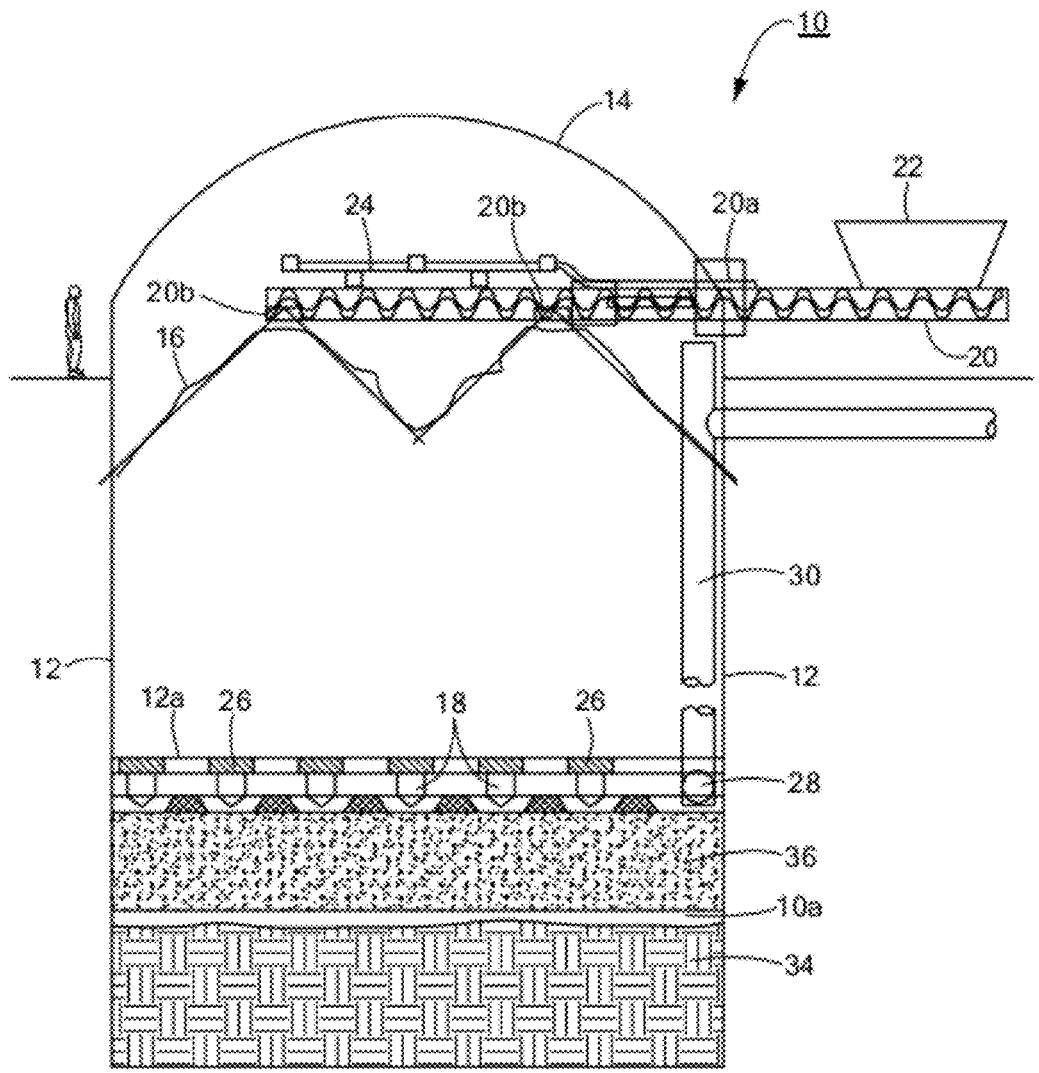
FIG. 2 shows a cross-sectional view of a subterranean alternating digester system according to embodiments of the present invention.
Figure 3:
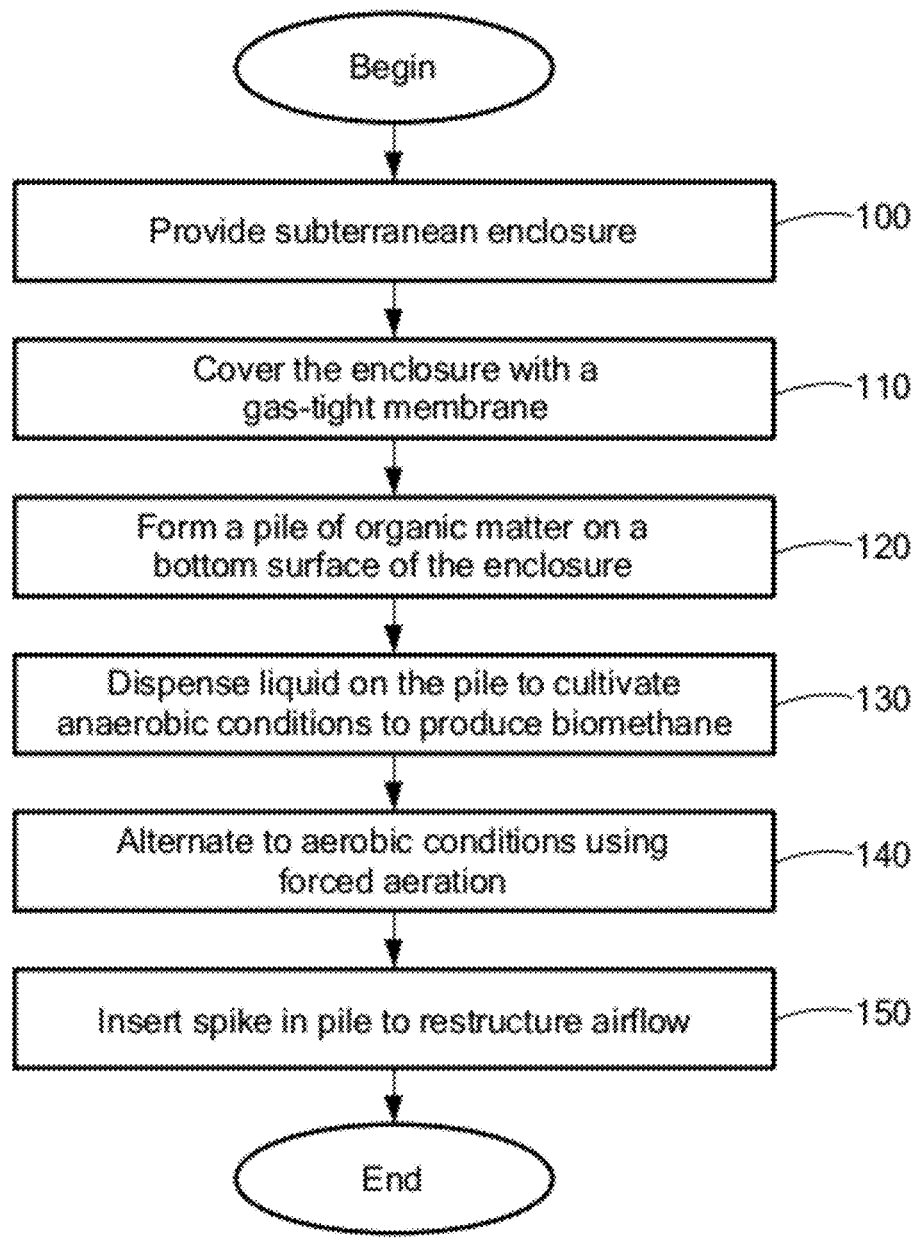
FIG. 3 shows a process of alternating subterranean digesting according to embodiments of the present invention.

FIGS. 1 and 2 schematically show a plan view and a cross-sectional view, respectively, of a subterranean alternating digester system 10 and FIG. 3 shows a process of alternating subterranean digesting according to embodiments of the present invention. Referring to FIG. 3, the process begins at step 100 in which a subterranean enclosure 12 is provided. As shown in FIGS. 1 and 2, the subterranean enclosure 12 is configured to hold organic matter and may be constructed of steel sheeting or sheetpiling, pre-cast concrete panels with water tight joints, or cast-in-place concrete, or other structural elements designed to withstand subterranean earth pressure and contain the digesting material.

In step 110, the enclosure is covered with a flexible, removable, gas-tight membrane 14. The membrane cover 14 has a gas-tight seal that seals the membrane cover 14 to the perimeter of the subterranean enclosure 12. The cover 14 prevents methane and fugitive odor release and also helps to prevent evaporation loss. As known by those skilled in the art, impermeable covers suitable for use as geomembranes may include High-Density Polyethylene (HDPE), Low-Density Polyethylene, Polypropylene, XR-5® (a woven synthetic fabric of DuPont Dacron Polyester) and periplastid reticulum (PPR) membranes and other flexible membrane materials.

In step 120, a pile 16 of the organic matter is formed on a bottom surface 12a of the subterranean enclosure 12. As shown in FIG. 2, the bottom surface 12a has a series of conduits 18. Details of the conduits 18 and their function will be discussed in more detail below. Preferably, the organic matter includes larger, oversized particles. During periods when larger particle materials are unavailable, the feedstock may be amended with screening oversized material, large woody particles cast off in the screening process, bark, and similar forest product residuals. The removal of the oversized particles may be accomplished at the final screening process after the composting process is complete. The oversized particles may include brush, branches, waxed or un-waxed corrugated cardboard boxes, dimensional wood, pallets, and/or crating. Preferably, the feedstock is a mixture of incoming organic matter, screening oversized particles and woody materials. The feedstock also, preferably, includes high-carbon amendments of at least about 95% carbon. The high-carbon amendments may include cedar bark, wood, sawdust and/or paper.

Because oversized particles are used, initial grinding of the feedstock is eliminated and brush, branches, dimensional wood, broken pallets, paper bags with waste, plastic bags with waste, and crating may be directly and immediately placed into the process without particle size reduction allowing for more rapid feedstock receiving and preparation. The use of oversized particles, along with a pile restructuring apparatus, also eliminates the need for pile turning during the digestion process. The pile restructuring apparatus or spike is discussed in more detail below. As a result, costs and emissions are significantly reduced. Because the un-ground feedstock is lower in bulk density and higher in porosity due to the inclusion of the larger particles, a deeper pile may be used than is commonly used in composting practice. For example, the pile of organic matter may be initially formed with an average height of about 15-25 feet. Thus, embodiments of the present invention provide more cost efficiency than other systems (e.g., approximately $30 per ton processed versus approximately $60 per ton processed) and allow for more seasonal composition, volume, and moisture variations through the use of a deeper pile and the addition of the high-carbon amendments in the pile. For example, the pile may have an initial density of no greater than about 700 pounds per cubic yard with a minimum porosity of about 50% by volume. The pile may also have a density ranging from about 650 to about 850 pounds per cubic yard over the entire residence time.

As shown in FIGS. 1 and 2, the organic matter may be fed into the enclosed space created by the subterranean enclosure 12 and the gas-tight membrane 14 by means of a completely enclosed and gas-tight screw conveyor 20. The conveyor 20 may have a pivot point 20a and multiple discharge chutes 20b. For example, FIG. 1 shows the conveyor 20 in four different positions and FIG. 2 shows the conveyor 20 with two discharge chutes, although multiple positions and discharge chutes may be used. The conveyor 20 may be made gas-tight by means of a resident plug of organic materials in the enclosed screw and housing. The conveyor 20 may include a feed hopper 22 and the screw in the conveyor 20 may determine the maximum particle size of the organic material by means of a natural shearing action and may open any bagged waste material. Although the above discussion discloses that the enclosure 12 is covered with the gas-tight membrane 14 before the pile 16 of organic matter is formed in the enclosure, the pile may also be formed in the enclosure first and then the enclosure 12 covered with the gas-tight membrane 14. Similarly, the pile may be formed in the enclosure first, then the enclosure 12 covered with the gas-tight membrane 14, and then additional organic matter may be fed into the enclosure 12. Thus, the feeding schedule of the conveyor 20 may be continuous, intermittent, or even seasonal, and the digestion pile may be built over time.

Referring again to FIG. 3, in step 130, a liquid percolation system 24 irrigates the top of the pile with liquids. As shown in FIG. 2, the irrigation system 24 may be coupled to the conveyor 20 or may be formed in a top portion of the enclosure 12 (not shown). The liquid to be dispensed on the pile may contain nutrients, buffering, and alkalinity to cultivate and maintain efficient methanogenesis within the organic matter. During this anaerobic phase of the process, liquids from the pile (e.g., produced from the digestion process of the organic matter or from excess liquids dispensed from the irrigation system) may be collected in the conduits 18 at the bottom surface 12a of the enclosure 12.

Figure 4:
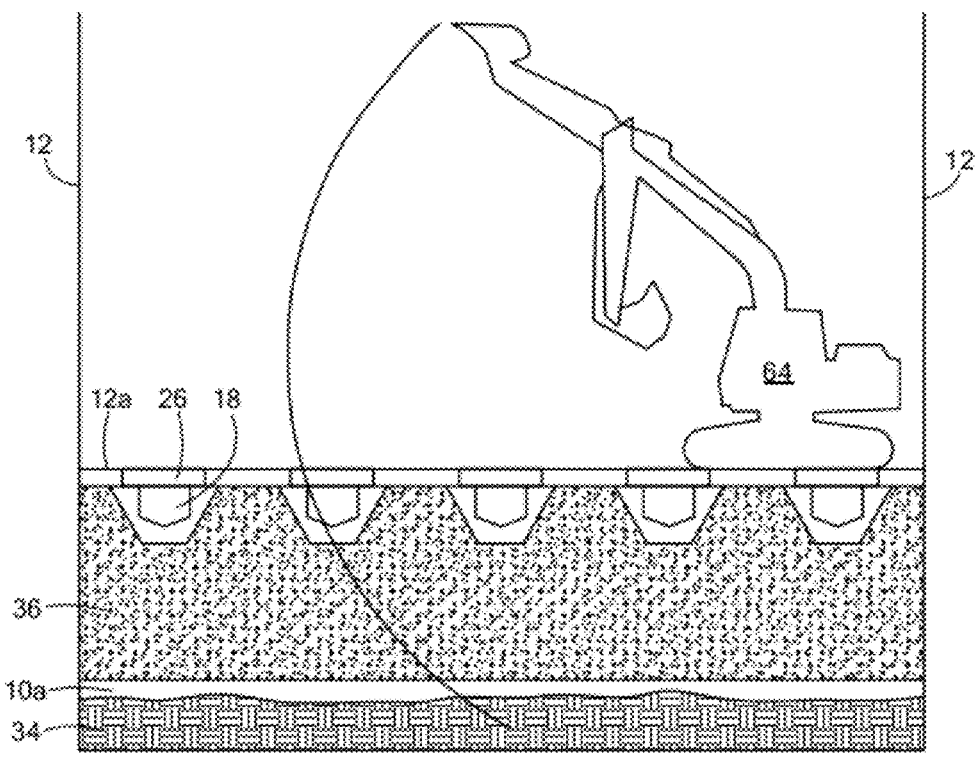
FIG. 4 shows a cross-sectional view of a bottom surface of a subterranean alternating digester system with conduits according to embodiments of the present invention.
Figure 5:
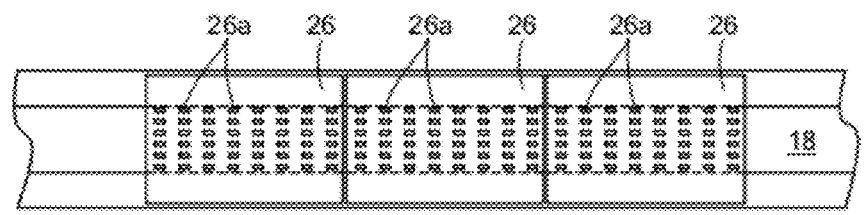
FIG. 5 shows a plan view of a covered conduit with channel cover plates according to embodiments of the present invention.

The conduits 18 may be channels formed in the bottom surface 12a, such as shown in FIGS. 2 and 4, or may be pipes placed on the bottom surface or in channels formed in the bottom surface (not shown). The pipes have holes that allow fluid to flow from an area outside of the pipe to within the pipe. When channels are used, the series of conduits 18 may each have one or more channel cover plates 26. As shown in greater detail in FIG. 5, each channel cover plate 26 may include openings 26a that allow the percolate and fluid from the pile 16 to flow into each conduit 18. The channel cover plate 26 may be made of various materials, preferably configured to withstand the forces of the pile and a machine, such as an excavator, that may be placed on the bottom surface 12a of the enclosure 12 when the digester batch is being removed. The conduits 18 may be spaced any distance apart from one another, e.g., about 8 feet apart, and may be formed of various materials, e.g., constructed of cast in place concrete. For example, each channel cover plate 26 may be about 48"×75" and the openings 26a may be about 1.5"×3" with 3" spacing and 6" spacing between openings. Alternatively, a layer of porous material designed to withstand the forces of the pile and a machine 64, such as an excavator, that may be placed on the bottom surface 12a of the enclosure 12 when the digester batch is being removed may be used to convey the liquid at the bottom of the enclosure.

As shown in FIGS. 1 and 2, the conduits 18 collect the percolate and fluid from the pile 16 and a submersible pump 28 pumps the liquid through a vertical manifold 30 to a liquid digester 32 adjacent to the digester system 10. The irrigation system 24 is in fluid communication with the liquid digester 32. The vertical manifold 30 may be formed of various materials, e.g., concrete, steel, or HDPE pipe. The liquid stored in the liquid digester 32 may consist of hydrolyzed liquids from the pile and make up water. The liquid is provided to the pile 16 and is collected through the conduits 18 such that a continuous production of biomethane occurs. The liquid in the irrigation system 24 may be maintained at a desired temperature to control the interior temperature in the digester enclosure 12. For example, the liquid may be heated in the liquid digester 32 or in the pipes in the irrigation system 24. When the percolate recovery and return system is operating and temperatures in the liquid and digester enclosure 12 are maintained in the optimum range, the production of biomethane increases significantly.

The biomethane production rate is measured for methane content and gross volumetric biogas production. Longer residence time, higher temperatures, and efficient liquid to organic matter contact (during percolation) are factors that increase actual biomethane yield. An example of this embodiment would be 6 months of residence time, a uniform 100° F. digester temperature, and an initial bulk density of 600-700 lbs per cubic yard. The biogas produced may be recovered from the top portion of the enclosure 12 and captured for later use.

As shown in FIGS. 2 and 4, the digester system 10 may also include a lower surface 10a formed on the native soil 34 and beneath the conduits 18. For example, the bottom surface 12a of the enclosure 12 and lower surface 10a of the system 10 may be constructed of concrete. The lower surface 10a of the system may be installed underwater as a tremie concrete plug to exclude groundwater and facilitate construction of the digester system 10 in areas of high groundwater. Between the bottom surface 12a and the lower surface 10a, a coarse (porous) mineral aggregate layer or other porous material 36 may be used between the surfaces, creating a leak detection zone. The leak detection zone may include a submersible pump 38 that pumps any recovered liquid to a liquid storage tank 40 adjacent to the digester system 10, as shown in FIG. 1. The recovered liquid may be groundwater that leaks upward from below the lower surface 10a or digester liquid that leaks downward from the digester enclosure 12, or a combination of both. After characterizing the liquid, the liquid can be either reused or disposed of depending upon its quality.

Figure 7:
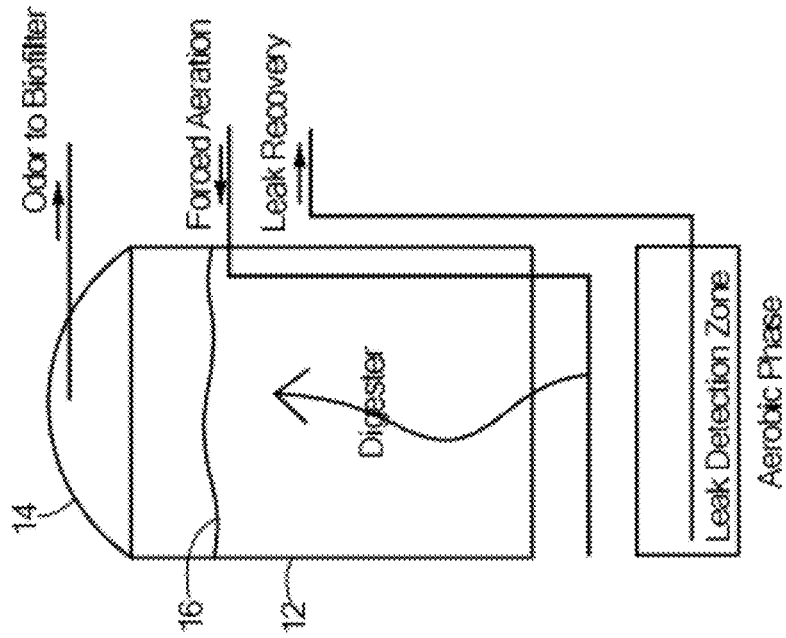
FIG. 7 schematically shows an aerobic phase in the alternating subterranean digestion system according to illustrative embodiments of the present invention.
Figure 6:
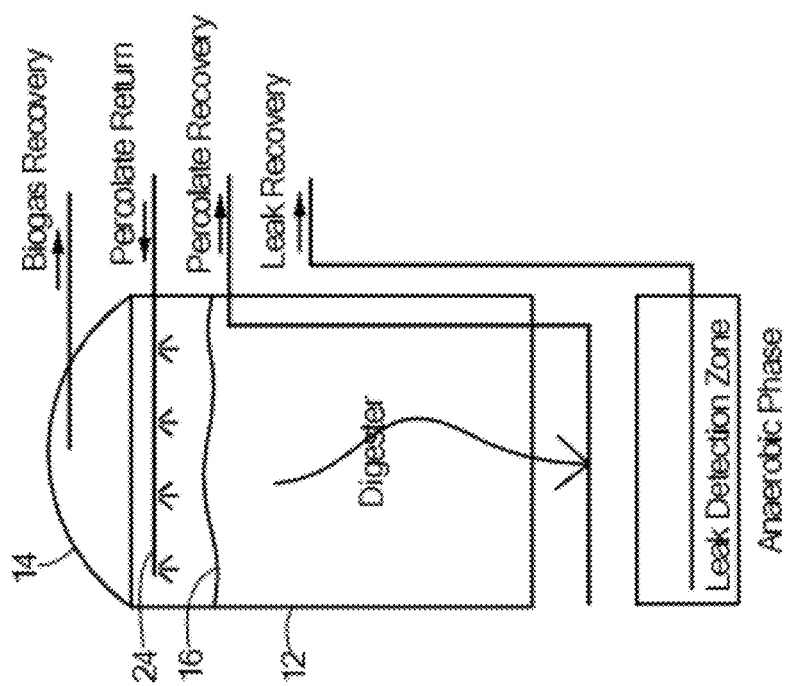
FIG. 6 schematically shows an anaerobic phase in the alternating subterranean digestion system according to illustrative embodiments of the present invention.

Referring again to FIG. 3, in step 140, the process then alternates to an aerobic environment for subsequent aerobic composting when the desired biomethane yield has been achieved. This is accomplished by turning the liquid irrigation system 24 off and removing all excess liquid from the system 10. Then, air is forced into the digester enclosure 12 using one or more pressure blowers or fans 42. The pressure fan 42 is configured to provide air flow through the conduits 18 such that a positive air pressure is formed at the bottom of the pile 16 forcing air through the pile and causing heat and moisture to exhaust out of the top of the pile 16. FIGS. 6 and 7 schematically show the flow of liquids and air in the anaerobic phase and the aerobic phase of the process. The airflow rate may vary from about 0.5 cfm per cubic yard to about 3.0 cfm per cubic yard. The exhaust air escaping from the top of the pile is hot (around 120-175° F.), odorous, and saturated.

Figure 8A:
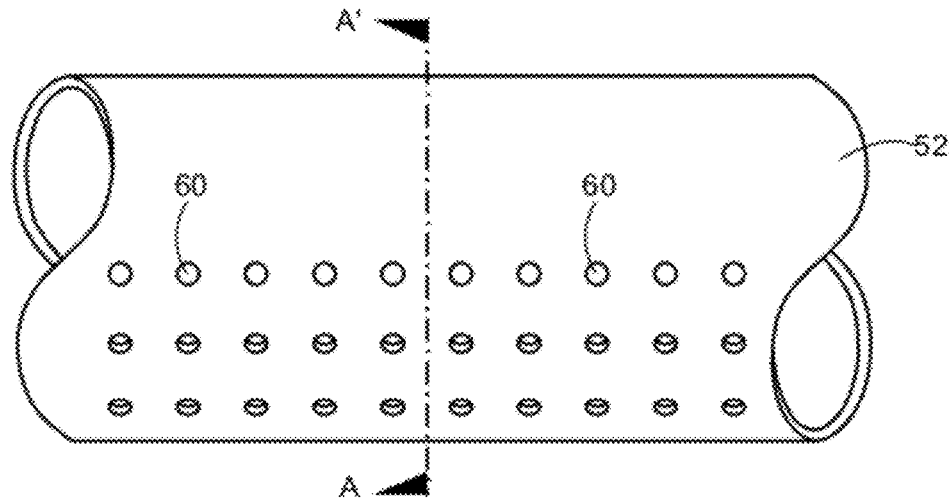
FIG. 8A schematically shows a side-view of a biofilter pipe according to embodiments of the present invention.
Figure 8B:
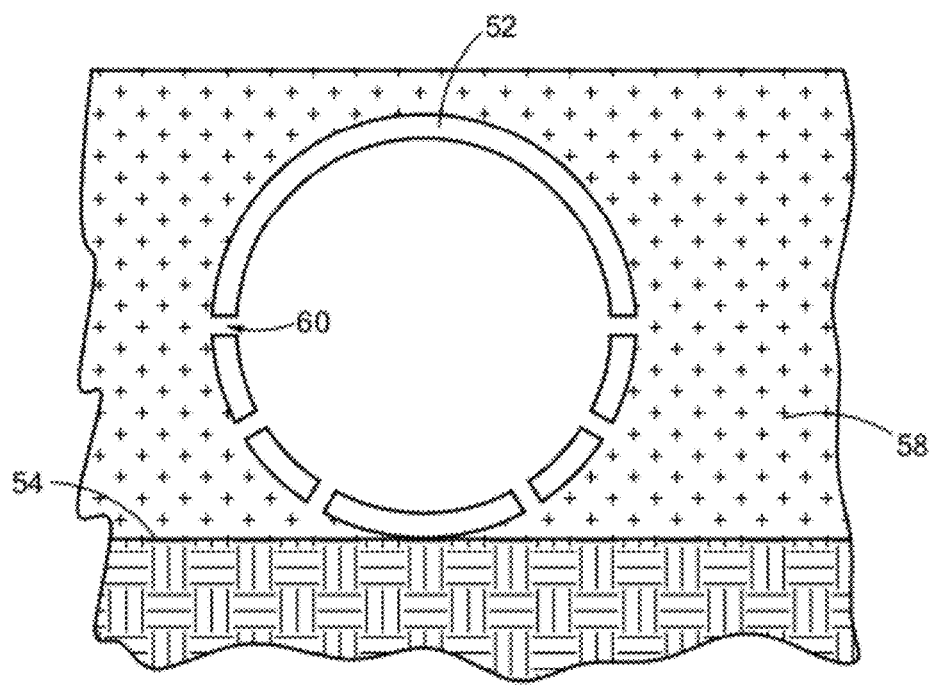
FIG. 8B schematically shows a cross-sectional view of a biofilter pipe along line A-A of FIG. 8A within biofilter material.
Figure 9:
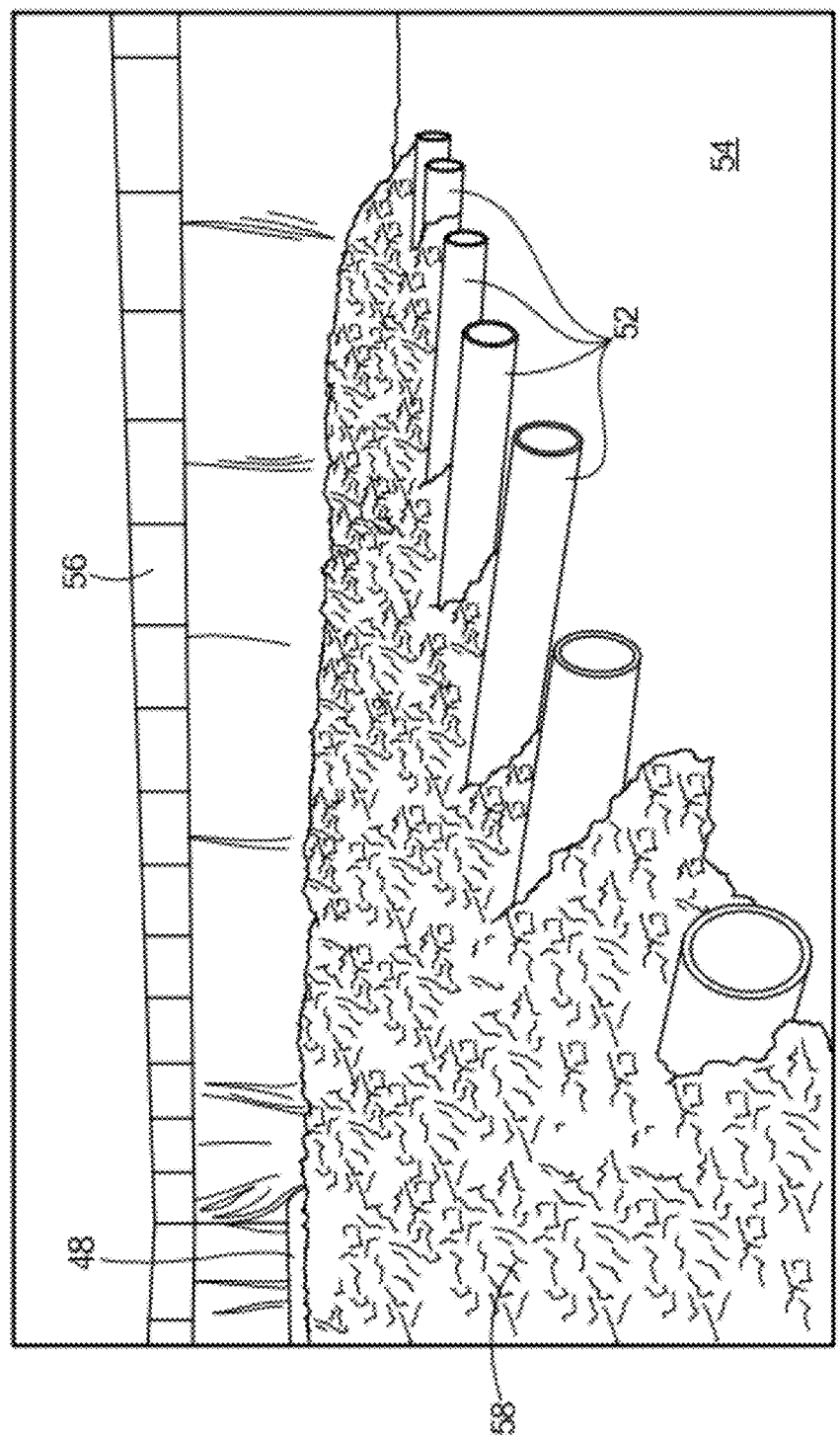
FIG. 9 shows biofilter pipes placed on top of a biofilter surface within a biofilter enclosure and surrounded by biofilter media according to embodiments of the present invention.

The digester system 10 may further include a biofilter system 50 in fluid communication with the top portion of the enclosure 12 such that the air and moisture withdrawn from the pile is transported to the biofilter 50 for exhaust treatment. For example, as shown in FIG. 1, the exhaust may be captured and collected by one or more exhaust fans 44 and discharged through an air manifold 46 in fluid communication with the top portion of the enclosure 12. The air manifold 46 is in fluid communication with a biofilter manifold 48, which transports the exhaust to the biofilter 50 which is used for emission or odor control. One or more ventilation fans 51 may also be in fluid communication with the biofilter manifold 48, which may allow ambient air to be blended in with the exhaust before going to the biofilter 50, to help with the temperature and moisture control of the biofilter air entering the biofilter system 50. The biofilter manifold 48 is also in fluid communication with a series of biofilter pipes 52, which are disposed on or in a biofilter surface 54 surrounded by a biofilter enclosure 56. The biofilter manifold 48 may run through an opening formed in the biofilter enclosure 56. The biofilter enclosure 56 is configured to hold biofilter media 58 formed around and on top of the biofilter pipes 52. FIGS. 8A and 8B schematically show a side-view and cross-sectional view, respectively, of one illustrative biofilter pipe 52. As shown, each of the biofilter pipes 52 has holes 60 that allow fluid to flow from within the biofilter pipe 52 to an area outside of the pipe which contains the biofilter media 58. Each of the biofilter pipes 52 may be placed on top of the biofilter surface 54, such as shown in FIG. 9, or may be placed within channels (not shown) formed within the biofilter surface 54.

Figure 10:
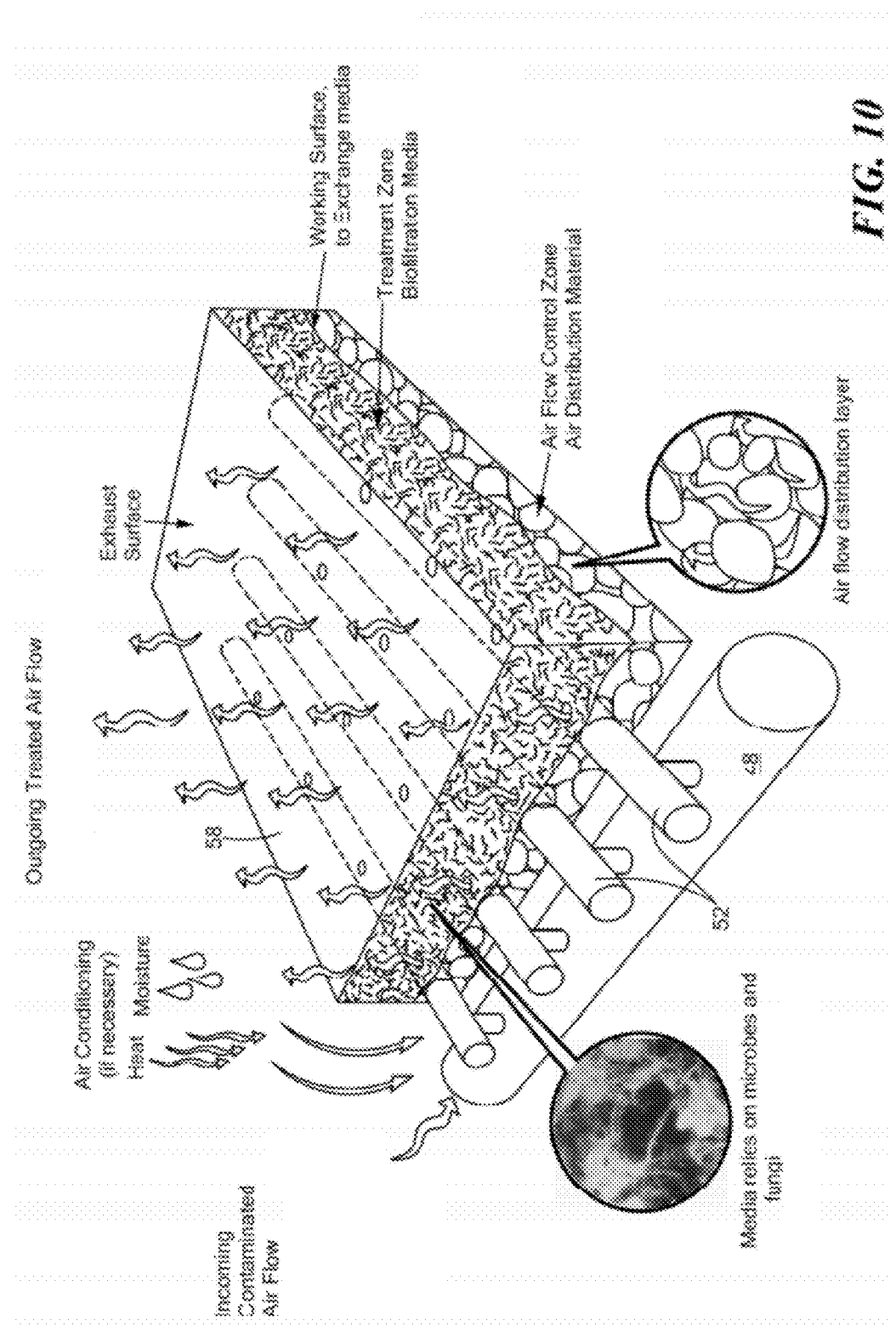
FIG. 10 schematically shows an illustrative biofilter system that may be used with embodiments of the present invention.

As known by those skilled in the art, the biofilter media 58 may be composed of various materials and layers, such as shown in FIG. 10. For example, the biofilter media 58 may include shredded wood and bark, preferably about 75% wood and about 25% bark. Other acceptable green materials may include plant leaves, needles, and grass, although preferably these are no more than about 2% by wet weight of the biofilter media. Dimensional wood, stumps, trees, clean plywood, and clean particle board or other materials may also be used. Preferably, the biofilter media 58 includes at least about 60% organic matter, a maximum TKN nitrogen of no more than 0.35%, a moisture content of between about 35 to about 60%, and combined nitrate and ammonium concentrations that are less than about 100 ppm. The biofilter media 58 also preferably includes at least about 90% by weight of particle sizes ranging from about 1.0 to about 4.0 inches, with less than about 10% by weight of particle sizes ranging less than about 1.0 inch and less than about 5% by weight of particle sizes ranging greater than about 4.0 inches.

Figure 11:
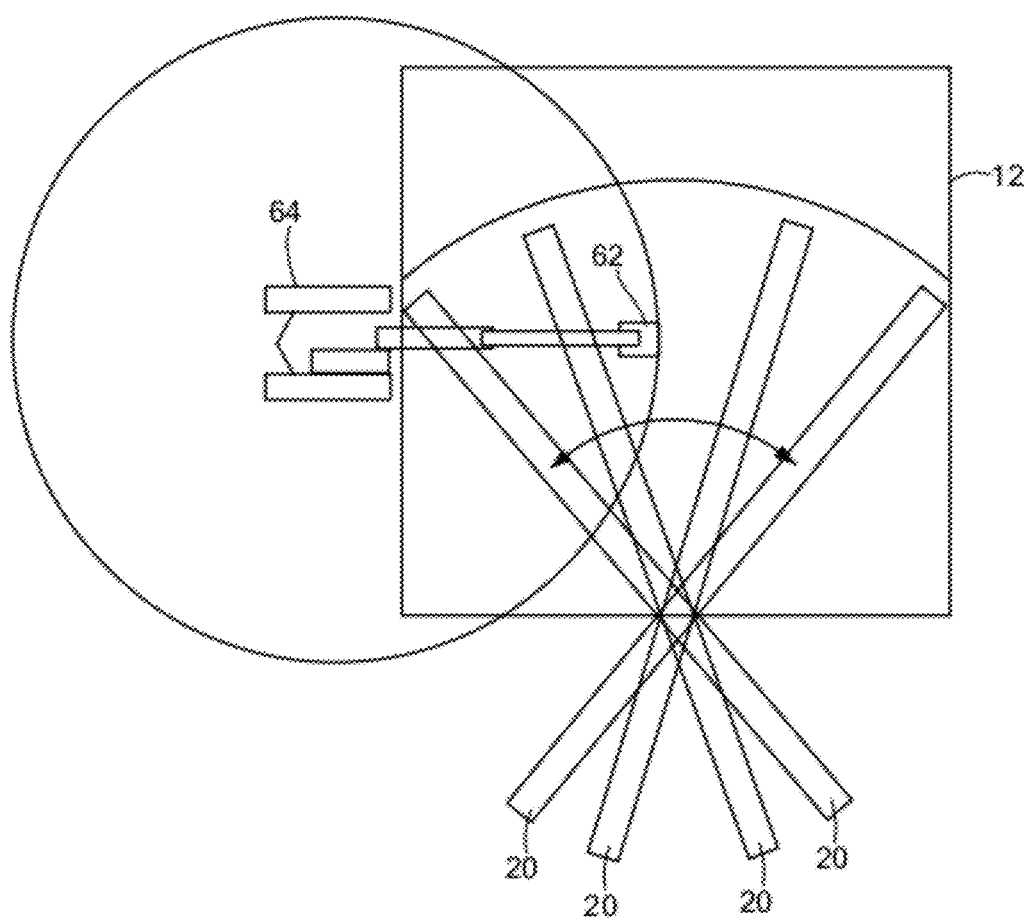
FIG. 11 shows a plan view of the digester enclosure with pivoting screw conveyor and an excavator outside the enclosure during pile restructuring or removal according to embodiments of the present invention.
Figure 12:
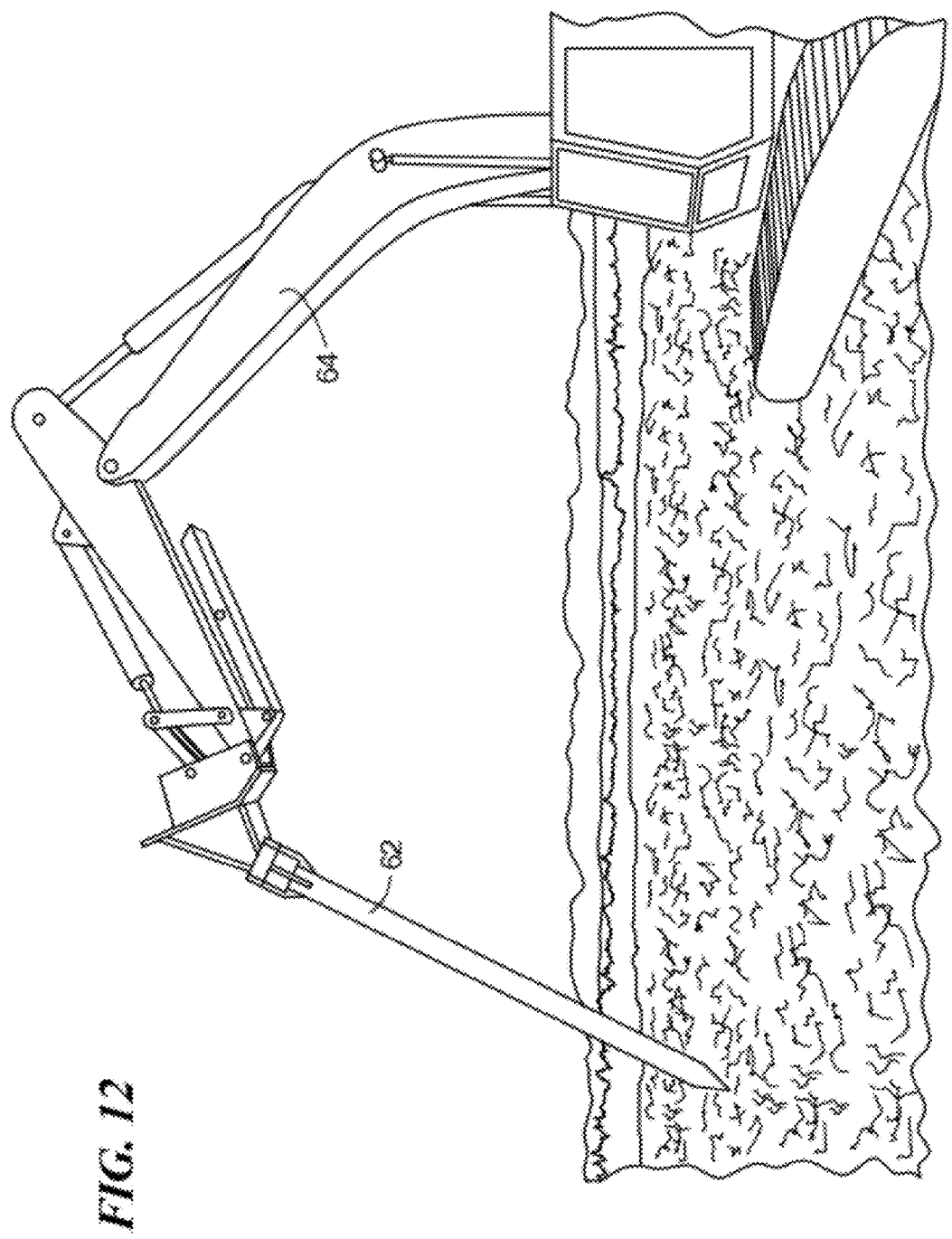
FIG. 12 shows a spike attached to a machine according to embodiments of the present invention.
Figure 13:
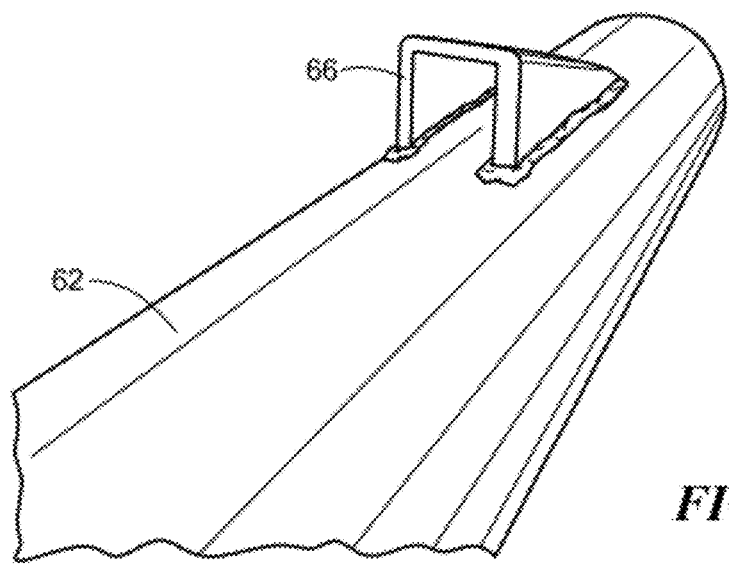
FIG. 13 shows a perspective view of a portion of the spike with a sampling corbel according to embodiments of the present invention.
Figure 14:
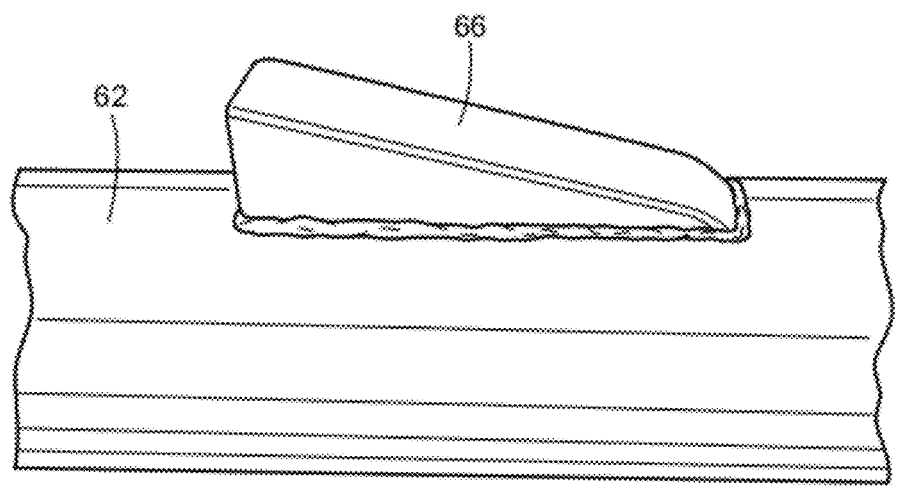
FIG. 14 shows a side-view of the sampling corbel shown in FIG. 13.

Referring again to FIG. 3, in step 150, the process further includes temporarily removing the membrane cover 14 after aerobic composting has been started and inserting a pile restructuring apparatus or spike 62 in the pile 16 at designated areas and times in order to form air shafts in the pile. The air shafts repair uneven airflow allowing substantially uniform aerobic conditions in the pile. As shown in FIGS. 11 and 12, the spike 62 may be mounted on a machine 64, such as an excavator or loader, which may be positioned around the enclosure 12. The spike 62 has a long shaft and may include a sampling corbel 66 attached on a side of the spike toward its end. In operation, the machine moves around the top of the enclosure 12 and punctures the pile with the spike 62 at designated areas leaving vertical air shafts throughout the pile. The air shafts may be formed in a uniform array of shafts across the pile or in an uneven pattern, e.g., in designated areas where more aerobic conditions are needed. For example, the air shafts may be spaced about 6 feet apart from the center of one shaft to the center of another. Preferably, the spike 62 is long enough so that the air shafts are formed through at least half the height of the pile. For example, for a pile having an initial height of about 25 feet, the spike may be about 13 feet long and have about an 8 inch diameter. The sampling corbel 66 allows a small sample of the lower horizon of the pile to be brought to the surface for observation and mapping of the lower horizon. The inspection of the sample may include a visual inspection of the moisture, color, texture, odor, and/or temperature of the organic matter. The observations and mapping may be recorded. This information may then be used to adjust airflow through the pile. Forming the array of air shafts across the pile 16 with the spike 62 may be done one or more times during the composting phase of the process, preferably about once for a pile having a composting process of about one month. The use of the spike 62 allows the organic matter in the pile 16 to have sufficient aerobic conditions for the composting process without the need for turning (tearing down and rebuilding) the pile. Higher porosity, volatile solids, nitrogen, and airflow are factors that increase the rate of composting. An example is about 1 month of residence time, an initial 160° F. digester temperature declining to 120° F., and an initial bulk density of 700-800 lbs per cubic yard at the beginning of composting.

Figure 15:
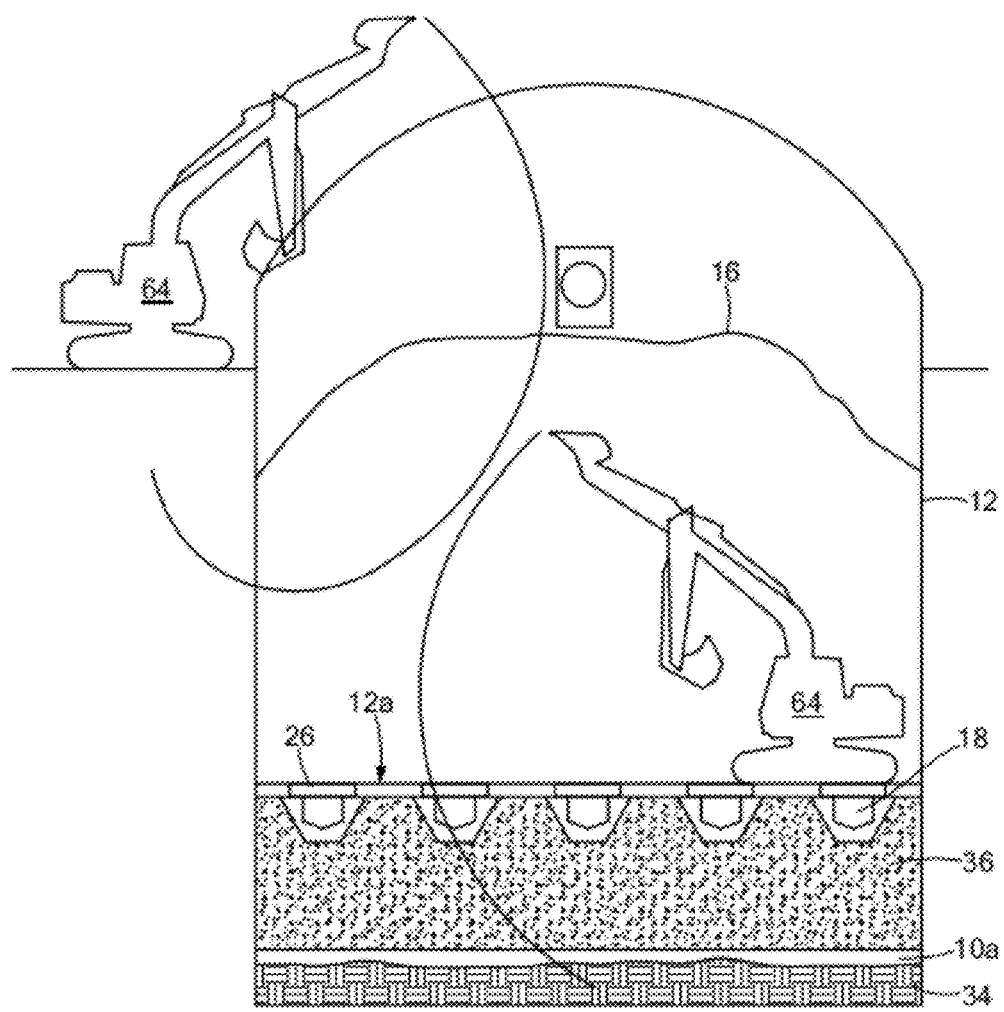
FIG. 15 schematically shows various locations of a machine during pile restructuring or removal of the organic matter at the end of the alternating subterranean digesting process according to embodiments of the present invention.

When a desired temperature drop has been achieved or a desired amount of biomethane has been produced, the digestion process is complete and the digester batch can be removed. FIG. 15 schematically shows various locations of a machine 64, such as a track styled hydraulic excavator or loader, during pile restructuring or removing of the organic matter at the end of the alternating subterranean digesting process. For example, a hydraulic excavator with approximately 30,000 lbs operating weight and approximately 100 hp may be used. After removal, the batch can be aged and then screened for sale as a compost or soil product. After removal of the batch, the bottom surface 12*a* of the enclosure 12 and pumps may be cleaned and serviced.

Although the above discussion discloses various exemplary embodiments of the invention, it should be apparent that those skilled in the art can make various modifications that will achieve some of the advantages of the invention without departing from the true scope of the invention.

What is claimed is:

1. An alternating anaerobic and aerobic digestion system comprising:
    a subterranean enclosure configured to hold organic matter, the enclosure having a plurality of conduits in a bottom surface of the enclosure;
    an irrigation system configured to dispense a liquid from a top portion of the enclosure and to recover a percolated liquid from a bottom portion of the enclosure;
    a ventilation system configured to provide air flow to the bottom portion of the enclosure;
    a leak detection zone below the bottom surface of the enclosure configured to collect and recover fluid, wherein the fluid includes groundwater that leaks upward, digester liquid that leaks downward from the enclosure, or a combination thereof; and
    a gas-tight membrane cover configured to cover the enclosure and to store gas produced during digestion.

2. The system of claim 1, further comprising:
    a spike configured to form air shafts in the organic matter.

3. The system of claim 2, wherein the spike further includes a sampling corbel on a side of the spike near its end.

4. The system of claim 1, wherein the ventilation system further includes an air outlet in the top portion of the enclosure, the system further comprising:
    a biofilter system in fluid communication with the air outlet of the ventilation system, the air outlet configured to transport heat, odor, and moisture from the top portion of the enclosure to the biofilter system.

5. The system of claim 1, wherein the plurality of conduits are formed by pipes placed on the bottom surface or by channels formed in the bottom surface and covered with channel cover plates.

6. The system of claim 1, further comprising:
    a screw conveyor configured to dispense the organic matter into the enclosure, wherein the screw conveyor includes two or more discharge chutes.

7. The system of claim 6, wherein the screw conveyor is coupled to a portion of the irrigation system that is configured to dispense the liquid on the organic matter.

8. A method of alternating anaerobic and aerobic digestion, the method comprising:
    providing a subterranean enclosure configured to hold organic matter;
    covering the enclosure with a gas-tight membrane;
    forming a pile of the organic matter on a bottom surface of the enclosure, the bottom surface having a plurality of conduits;
    dispensing a liquid on the pile and capturing biogas from a top portion of the enclosure;
    providing air flow to a bottom portion of the pile so that heat, odor, and moisture escape from a top portion of the pile;
    forming a porous, mineral aggregate layer below the bottom surface to form a leak detection zone configured to collect and recover fluid, wherein the fluid includes groundwater that leaks upward, digester liquid that leaks downward from the enclosure, or a combination thereof; and
    inserting a spike in the pile at designated areas and times in order to form air shafts in the pile.

9. The method of claim 8, further comprising:
    recovering a percolated liquid from beneath the pile and using at least a portion of the percolated liquid to dispense on the pile.

10. The method of claim 8, further comprising:
    forming an air outlet in the top portion of the enclosure; and
    forming a biofilter system in fluid communication with the air outlet, the air outlet configured to transport the heat, odor, and moisture from the top portion of the enclosure to the biofilter system.

11. The method of claim 8, further comprising:
    pumping the liquid from the leak detection zone to a liquid storage tank.

12. The method of claim 8, further comprising:
    providing a screw conveyor configured to dispense the organic matter into the enclosure, wherein the screw conveyor includes two or more discharge chutes.

13. The method of claim 12, wherein the screw conveyor is also configured to dispense the liquid on the pile.

14. The method of claim 8, wherein the organic matter includes oversized particles greater than 6 inches.

15. The method of claim 8, wherein the pile is formed with a height of at least about 20 feet.

16. The method of claim 8, wherein the plurality of conduits include pipes placed on the bottom surface of the enclosure.

17. The method of claim 8, wherein the plurality of conduits include channels formed in the bottom surface and covered with channel cover plates.

18. The method of claim 8, wherein the organic matter includes high-carbon amendments of at least about 95% carbon.

19. The method of claim 18, wherein the high-carbon amendments include cedar bark, wood, sawdust, paper, or a combination thereof.

20. The method of claim 8, further comprising taking a sample of the organic matter with the spike in order to analyze a lower portion of the pile.

21. A method of forming an alternating anaerobic and aerobic digestion system, the method comprising:

providing a subterranean enclosure configured to hold organic matter;

forming a plurality of conduits in a bottom surface of the enclosure;

forming an irrigation system configured to dispense a liquid from a top portion of the enclosure and to recover a percolated liquid from a bottom portion of the enclosure;

forming a ventilation system configured to provide air flow to the bottom portion of the enclosure;

forming a leak detection zone beneath the bottom surface of the enclosure configured to collect and recover fluid, wherein the fluid includes groundwater that leaks upward, digester liquid that leaks downward from the enclosure, or a combination thereof; and covering the enclosure with a gas-tight membrane cover.

22. The method of claim 21, further comprising:

providing a spike configured to form air shafts in the organic matter.

23. The method of claim 21, wherein the ventilation system further includes an air outlet in the top portion of the enclosure, the method further comprising:

forming a biofilter system in fluid communication with the air outlet of the ventilation system, the air outlet configured to transport heat, odor, and moisture from the top portion of the enclosure to the biofilter system.

24. The method of claim 21, wherein the plurality of conduits are formed by placing pipes on the bottom surface or are formed by forming channels in the bottom surface and covering with channel cover plates.

25. The method of claim 21, further comprising:

providing a screw conveyor configured to dispense the organic matter into the enclosure, wherein the screw conveyor includes two or more discharge chutes.

26. The method of claim 25, wherein the screw conveyor is coupled to a portion of the irrigation system that dispenses the liquid on the pile.

27. The method of claim 21, further comprising taking a sample of the organic matter with the spike in order to analyze a lower portion of the pile.

* * * * *